United States Patent [19]
Chandar et al.

[11] Patent Number: 5,811,112
[45] Date of Patent: Sep. 22, 1998

[54] OIL-IN-WATER COSMETIC EMULSIONS CONTAINING A STABILIZED PROTEASE

[75] Inventors: Prem Chandar, Closter; Norman Kramer Richardson, Rockaway; Alyse Battaglia, Hoboken; Karla Jean Cicciari, Ramsey; Kara Newell El-Kadi, Chester, all of N.J.

[73] Assignee: Chesebrough-Pond's USA Co., Division of Conopco Inc., Greenwich, Conn.

[21] Appl. No.: 866,916

[22] Filed: May 30, 1997

[51] Int. Cl.⁶ ...................................................... A61K 7/00
[52] U.S. Cl. ............................... 424/401; 424/59; 424/63; 424/65; 424/69; 424/94; 424/94.63; 514/772.3; 514/782; 514/783; 514/938
[58] Field of Search ................................ 424/401, 59, 63, 424/65, 69, 94.3, 94, 94.63–94.67; 514/772.3, 782, 783, 770, 970, 938

[56] References Cited

U.S. PATENT DOCUMENTS

| | | | |
|---|---|---|---|
| 4,906,396 | 3/1990 | Falholt et al. | 252/174 |
| 5,434,069 | 7/1995 | Tsaur et al. | 435/188 |
| 5,439,935 | 8/1995 | Rawlings et al. | 514/451 |
| 5,441,660 | 8/1995 | Tsaur et al. | 252/95 |
| 5,545,402 | 8/1996 | Watkinson | 424/94.63 |
| 5,554,366 | 9/1996 | Rawlings et al. | 424/78.03 |

FOREIGN PATENT DOCUMENTS 6239735   8/1994   Japan .

*Primary Examiner*—Neil S. Levy
*Attorney, Agent, or Firm*—Rimma Mitelman

[57] ABSTRACT

Cosmetic oil-in-water emulsions which are intended to be left on the skin after application (not rinsed off) the emulsions incorporating a stabilized protease. The cosmetic emulsions useful in treatment of dry, flaky, rough, aged, wrinkled or cellulotic skin.

10 Claims, No Drawings

OIL-IN-WATER COSMETIC EMULSIONS CONTAINING A STABILIZED PROTEASE

FIELD OF THE INVENTION

Water-continuous emulsions for skin care containing a stabilized protease.

BACKGROUND OF THE INVENTION

Stabilization of enzymes has been well explored in the art of liquid laundry detergents. See for instance U.S. Pat. No. 4,906,396 (Fallout et al.), U.S. Pat. No. 5,434,069 (Tsaur et al.) and U.S. Pat. No. 5,441,660 (Tsaur et al.). Falholt and Tsaur describe compositions containing droplets of enzyme dispersed in a hydrophobic material. Tsaur teaches that such droplets must be further encapsulated within a polymeric shell, since the droplets alone do not attain sufficient enzyme stability.

By contrast, stabilization of enzymes in cosmetic compositions has been barely considered. The above-cited patents neither mention cosmetic compositions nor address the problem of providing stability to an enzyme in a cosmetic composition. Most cosmetic compositions are oil-in-water emulsions, which are intended to be left on the skin, not rinsed off (hence the term "leave on" compositions). Incorporation of enzyme droplets into such emulsions presents a problem of maintaining the stability of the enzyme in the droplets without disrupting the stability of an external emulsion.

Liquid detergents typically contain electrolytes (salts) and surfactants, each dissolved in an aqueous phase at a relatively high concentration. Salts and surfactants in combination with each other provide a necessary structure to support enzyme droplets in a detergent composition. Such structuring systems are not suitable for cosmetic "leave on" compositions. Salts and/or surfactants, especially when used at higher levels as in the detergents, would destabilize cosmetic "leave on" emulsions and would also be irritating to skin.

Thus, while enzyme droplets containing an enzyme dispersed in a hydrophobic carrier may feature in both liquid detergents and in the presently claimed cosmetic compositions, the environment of enzyme release in the two systems is so diverse, the chemical composition and physical characteristics of the detergent compositions and of the cosmetic compositions are so different, and the principles and skills in formulating laundry compositions and cosmetic compositions are so distinct, that it is difficult to extend the teachings in the liquid detergent art to the presently claimed cosmetic compositions.

Japanese Patent Application No. 6239735 (JP '735) describes a gelatin capsule containing an enzyme. The enzyme is dispersed in a liquid oily base and the resulting mixture is encapsulated in gelatin and subsequently treated further with acetaldehyde or propionaldehyde to insolubilize the gelatin capsule. The capsule is said to be useful as a scrubbing agent in liquid skin cleansing compositions. The capsule is also said to have a long-term stability. The serious drawback of JP '735 is that it is still addressed to cleansing compositions, not to oil-in-water cosmetic "leave-on" emulsions. It does not teach any ingredients external to the capsules, other than to say in general that the compositions are liquid cleansers. Also, the use of acetaldehyde or propionaldehyde presents safety concerns. The present invention provides a very different, safe and much less complex stabilization system for an enzyme in an oil-in-water "leave on" cosmetic emulsion.

Oil-in-water cosmetic emulsions containing proteases are known. U.S. Pat. Nos. 5,439,935 (Rawlings et al.); 5,554,366 (Rawlings et al.) and 5,545,402 (Watkinson et al.) describe cosmetic compositions containing various proteases for desmosome degradation and consequent treatment of dry flaky skin. The composition may optionally include an emollient, which may be selected from a long list of liquid and solid emollients, including some of the emollients which are used in the present invention. The Rawlings and Watkinson patents, however, do not address the enzyme instability problem and do not teach any enzyme stabilization systems.

The art discussed above does not provide a satisfactory enzyme stabilization system for an oil-in-water cosmetic emulsion.

SUMMARY OF THE INVENTION

The present invention includes an oil-in-water emulsion for a leave-on skin care composition, the emulsion comprising:

(a) from 1% to 10 wt. % of droplets comprising a solid anhydrous protease distributed in a hydrophobic carrier, wherein the carrier has a melting point in the range of from 30° C. to 80° C.;

(b) at least 60% of water;

(c) from 1% to 40 wt. % of an emollient which has a melting point in the range of from 30° C. to 80° C., wherein the emollient contains a hydrophobic hydrocarbon backbone and a hydrophilic polar headgroup, and wherein the emollient lowers the water activity of the emulsion to at least 0.99.

The invention also includes a cosmetic method of treating dry, or flaky, or rough, or cellulotic, or aged, or wrinkled skin, by applying to the skin the inventive composition.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

Protease

A protease suitable for use in the present invention must be in a solid (preferably powdered), anhydrous form. The term "anhydrous" as used herein means that the protease preparation contains less than 0.001%, and preferably less than 0.0001% by weight of the preparation, of water.

Suitable proteases can be of bacterial, mammalian, fungal or plant origin. Examples of mammalian proteases include stratum corneum thiol proteases, stratum corneum chymotrypsin-like and trypsin-like proteases, and stratum corneum cathepsin-D-like protease.

In a preferred embodiment, the protease has a Caseinolytic Activity of at least 900 GU/gram of the emulsion in order to deliver an optimum benefit to the skin. Caseinolytic Activity test is described in Example 3.

In order to minimize the level of incorporation of the protease in the emulsion so as to obtain high efficacy at optimum cost and low safety risks, the protease according to the present invention preferably fulfills the following requirements:

(1) it has an optimum activity between pH 5 and 9;

(2) it has a specific activity greater than $8 \times 10^5$ GU/gram of pure protease; and (3) it has a broad substrate specificity as defined by an independence of specificity on primary structure.

Specific activity is the number of glycine units resulting from the reaction of one gram of protease with casein. 1 GU (glycine unit) is defined as the amount of proteolytic enzyme which under standard incubation conditions degrades casein to produce an amount of terminal $NH_2$ groups equivalent to 1 microgram/mL of glycine.

Preferred protease is of bacterial or fungal origin, preferably the protease produced by Bacillus or Aspergillus, preferably by the following species of Bacillus or Aspergillus: *Bacillus subtilis, Bacillus licheniformis, Aspergillus oryzae, Aspergillus niger, Bacillus thermoproteolyticus* most preferably serine proteases or metalloprotease produced by these species. Most preferably, the protease has a specific activity of at least $8 \times 10^6$ GU/g of protease (measured at pH=8.0). Serine proteases or metalloproteases of bacterial origin have the highest specific activity and thus are most preferred for use in the present invention.

The inventive compositions include from 0.004 to 0.3 wt. %, preferably from 0.01 to 0.2 wt %, and most preferably from 0.05 to 0.15 wt % of a solid anhydrous protease.

Carrier

According to the present invention, the solid anhydrous protease is distributed in a hydrophobic carrier having a melting point in the range of from 30° C. to 80° C. Preferably, the melting point is in the range of from 35° C. to 65° C., most preferably from 45° C. to 60° C. The selection of a carrier having a melting point in this range is critical, in order to ensure that the droplets containing protease are friable under shear during application, yet have sufficient structure to stably hold the protease during storage.

Suitable compounds for use as a carrier include but are not limited to waxes which may be of mineral, vegetable, animal, insect, or synthetic origin. Examples include but are not limited to petrolatum wax, microcrystalline wax, paraffin waxes, ozokerite, carnauba wax, spermaceti, beeswax, silicone wax.

The hydrophobic carrier is employed in the inventive compositions in an amount of from 0.1 wt. % to 5 wt. %, by weight of the emulsion. The specific amount of the carrier depends on the amount of the protease that is being distributed in the carrier. Preferably, the amount of the carrier is in the range of from 0.5 wt. % to 2 wt. %, most preferably from 0.8 to 1.5 wt. %.

The inventive compositions contain from 1 wt. % to 10 wt. % of the droplets formed with the carrier and the protease, preferably from 2 wt. % to 8 wt. %, most preferably from 4 wt. % to 6 wt. %.

The size of the carrier/enzyme droplets in the inventive compositions is generally from 100 $\mu$M to 1,000 $\mu$M, preferably from 200 $\mu$M to 800 $\mu$M, most preferably from 400 $\mu$M to 600 $\mu$M.

Emollient

It has been discovered as part of the present invention that the identity of an emollient is critical to impart stability to the protease droplets in the cosmetic oil-in-water emulsions. Emollients suitable for use in the present invention are crystalline emollients which satisfy melting point and chemical structure requirements. The emollient suitable for use in the present compositions has a melting point in the range of from 30° C. to 80° C. The emollient having a melting point less than 80° C. can be easily melted during processing of the emulsion to assure uniform dispersion and, yet on cooling the emollient due to having a melting point greater than 30° C. will form a structure that maximally binds water to lower the water activity of the emulsion.

Furthermore, in order to effectively reduce water activity, the emollient must contain a hydrophobic hydrocarbon chain, typically containing from 12 to 24 carbon atoms, preferably from 14 to 22 carbon atoms, and a polar headgroup. The polar headgroup is selected from the group consisting of —OX and —COOX, where X is selected from the group consisting of hydrogen, an alcohol, a sugar group, an alkyl, and an alkenyl; and wherein the polar headgroup contains no more than 10 carbon atoms, preferably no more than 8 carbon atoms, and most preferably no more than 6 carbon atoms.

A single compound or a mixture of compounds may serve as a suitable emollient in the present invention.

Suitable emollients include but are not limited to: fatty acids, fatty alcohols, fatty acid esters of glycerol, fatty alcohol esters of glycerol, ethylene glycol, propylene glycol, lactyl lactate, fatty acid esters of sorbitan, fatty alcohol esters of sorbitan, and mixtures thereof. Most preferred emollients are selected from the group consisting of alcohol, sodium stearoyl lactylate, glycol stearate, stearic acid, cetyl phosphate and mixtures thereof.

The inventive compositions employ from 1 wt. % to 40 wt. % of an emollient, preferably from 4 wt. % to 15 wt. %, most preferably from 7 wt. % to 12 wt. % by weight of the emulsion.

Water

The inventive compositions are oil-in-water emulsions. The particular advantage of the inventive compositions is that the enzyme stability may be attained, even in the presence of the large amount of water. Consequently, the compositions typically contain at least 60 wt. % water, preferably from 60 wt. % to 95 wt. %, most preferably from 80 wt. % to 95 wt. % water.

According to the present invention, the water activity (which indicates the degree to which the water is unbound) is critical to maintain the stability of the enzyme, the water activity is no greater than 0.99, preferably is no greater than 0.98, most preferably is less than 0.97. The water activity within these boundaries is attained due to the presence of the specific emollient described above.

The inventive compositions may contain additional water-binding agents, such as glycerol, hydrophilic polymers (e.g., polyacrylate, polyacrylamide, carboxymethylcellulose), gums (e.g. xanthan gum, guar, sclerotium, carrageenan, pectin) and clays to ensure water activity values described above. Additional water-binding agents may be included in the inventive compositions at a level of 0.5–20 wt. %.

Making of the Composition

The inventive emulsions may be prepared as follows:

Preparation of the enzyme droplets

The hydrophobic carrier is heated until melted. Using an overhead mixer, the enzyme is slowly dispersed in the molten carrier (maintaining high temperature). The dispersion is cooled to room temperature and allowed to sit for 24 hours before further use. A polymer solution is preferably used to stabilize the dispersion. Suitable polymers are water-thickening polymers, typically selected from the group consisting of polyacrylates, gums, celluloses, and mixtures thereof. The polymer solution (desired polymer(s) in water) is made separately. A solution containing the emollients (e.g. glycerol, propylene glycol) is mixed and heated to 40°–80° C. Desired quantities of polymer solution and enzyme/carrier dispersion are weighed into a beaker. This mixture is homogenized (e.g. Arde Barinco Benchtop homogenizer) for 1–3 minutes. The warm gum/emollient mixture is then added and the emulsion is homogenized for 3–8 additional minutes.

The resulting enzyme droplets are preferably not further encapsulated (contrary to the teaching of the Tsaur detergent composition patent discussed in the background section above), in order to ensure rupture during the application of the inventive composition to the skin.

Preparation of the emulsion

The oil phase components (i.e. emollients, emulsifiers, oils, etc.) are mixed together and heated until melted. The water phase, containing any water-soluble components (i.e. humectants, thickeners, etc.) is heated to the same temperature with overhead mixing at 600–900 rpm. While mixing, the melted oil phase is poured into water phase and mixed for an additional 30–60 minutes at the same temperature. Preservatives are then added to the mixture and the heat is turned off. When the mixture reaches 45° C.–47° C., optional ingredients (colorants, fragrance, skin feel agents and heat sensitive ingredients) are added. The product is then allowed to cool to room temperature while mixing. Enzyme droplets, at the desired level, are then blended into the emulsion, either manually or with an overhead mixer.

Optional Ingredients $C_1$–$C_6$ alkanols are preferably excluded from the inventive compositions, to preserve the stability of the droplets in the inventive emulsions. Thus, the emulsions contain less than 1 wt. % of such alcohols, and preferably do not contain alcohols at all.

Surfactants, especially anionic and nonionic surfactants, are kept at a minimum in the inventive compositions, in order to preserve the stability of the enzyme droplets in the compositions. The inventive compositions preferably do not include more than 5 wt. % of surfactants, preferably not more than 2 wt. %. Anionic or nonionic surfactants that are limited, or preferably excluded, in the inventive compositions are as follows:

nonionic surfactants with a $C_{10}$–$C_{20}$ fatty alcohol or acid hydrophobe condensed with from 4 to 100 moles of ethylene oxide or propylene oxide per mole of hydrophobe; $C_2$–$C_{10}$ alkyl phenols condensed with from 4 to 20 moles of alkylene oxide; block copolymers (ethylene oxide/propylene oxide); and polyoxyethylene sorbitan as well as combinations thereof. Also, polyglycosides and saccharide fatty amides (e.g. methyl gluconamides) are preferably excluded.

anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Additional emollients, although such do not provide enzyme stability may be present. Examples include mineral oil, silicone oil, vegetable oils, isopropyl palmitate, isoparaffin.

The inventive emulsions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

The inventive compositions preferably include preservatives to protect compositions against the growth of potentially harmful microorganisms. Suitable preservatives include alkyl esters of p-hydroxybenzoic acid, hydantoin derivatives, propionate salts, and a variety of quaternary ammonium compounds. Preservatives will usually be employed in amounts ranging from about 0.1% to 2% by weight of the composition.

Other adjunct minor components may also be incorporated into the cosmetic compositions. These ingredients may include coloring agents, opacifiers and perfumes. Amounts of these other adjunct minor ingredients may range anywhere from 0.001% up to 20% by weight of the composition.

Stability

The stability of an enzyme in the inventive cosmetic emulsions is such that after 6 months storage at ambient temperatures (20°–25° C.) at least 10% of the initial enzyme activity is retained. Stability can be monitored via an accelerated stability test in which the emulsions are stored at 30° C. It is desirable that the emulsions maintain approximately greater than 30%, preferably 40% and most preferably 50% of the initial activity after two weeks of storage under the accelerated conditions described in Example 3 in order for the desired activity under ambient conditions to be maintained.

pH

The inventive emulsions have a pH in the range of from 4 to 9, preferably in the range of from 6 to 9.

Use of the Composition

The composition according to the invention is intended primarily as a product for topical application to human skin, especially as an agent for controlling or preventing dry, flaky, rough, cellulotic, aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin composition of the invention can be in any form, e.g. formulated as a lotion, a fluid cream, or a cream. The composition can be packaged in a suitable container to suit its viscosity and intended use by the consumer. For example, a lotion or fluid cream can be packaged in a bottle or a roll-ball applicator or a container fitted with a pump suitable for finger operation, or a dual compartment. When the composition is a cream, it can simply be stored in a non-deformable bottle or squeeze container, such as a tube or a lidded jar. The invention accordingly also provides a closed container containing a cosmetically acceptable composition as herein defined.

The following specific examples further illustrate the invention, but the invention is not limited thereto.

EXAMPLE 1

A series of emulsions were prepared having the compositions defined in Tables I and II below (A–K) and water activity measured.

The indicated ingredients were combined together and heated to 80° C., with overhead mixing, then allowed to cool with continuous stirring. Products were allowed to equilibrate for 24 hours before water activity measurements were taken. Water activities (Aw) were measured using the chilled mirror technique with an Aqua Lab, CX-2, with an accuracy of 0.003 Aw units.

Examples A–E (Table I) represent emulsions prepared from liquid emollients outside the scope of the invention. Example (F–K) represent emulsions containing crystalline emollients within the scope of the invention.

TABLE I

Emulsions prepared from liquid emollients and their water activities.

| Ingredient (%) | A | B | C | D | E |
|---|---|---|---|---|---|
| Mineral oil (Drakeol 9, Penreco) | 8.0 | 18.0 | — | 9.5 | 14.0 |
| Sunflower seed oil | — | — | 18.0 | — | — |
| Polyoxyethylene 20 sorbitan monolaurate (Tween 20, ICI) | 2.0 | — | 2.0 | — | — |
| Polyoxyethylene 20 sorbitan monooleate (Tween 80, ICI) | — | 2.0 | — | 0.5 | 1.0 |
| Polyacrylamide (Sepigel, Sepic) | 1.0 | 1.0 | 1.0 | 1.0 | 1.0 |
| distilled water | 89.0 | 79.0 | 79.0 | 89.0 | 84 |
| water activity (Aw) ----------------------> | 1.000 | 0.992 | 1.000 | 0.994 | 0.993 |

TABLE II

Emulsions prepared from crystalline emollients and their water activities

| | WT% | | | | | |
|---|---|---|---|---|---|---|
| Ingredient | F | G | H | I | J | K |
| Mineral Oil | — | — | — | — | — | 5 |
| Crystalline Emollients | | | | | | |
| Sodium stearoyl lactylate (Pationic SSL, RITA Corp.) | — | — | 1.0 | 0.5 | 1.05 | 1.0 |
| Glyceryl monostearate (Cutina GMS, Henkel) | 9.5 | 9.5 | 9.0 | 9.5 | 13.95 | 9.0 |
| Cetyl phosphate (Monofax 160, Mona Inc.) | — | 0.5 | — | — | — | — |
| Cetyl alcohol (Lanette 16, Henkel) | — | — | — | — | — | — |
| distilled water | 90.5 | 90 | 90 | 90 | 85 | 85 |
| water activity (Aw)----------------------> | 0.982 | 0.982 | 0.984 | 0.980 | 0.986 | 0.980 |

This example demonstrates that when the crystalline emollients within the scope of the invention we incorporated in a emulsion (Table II), they reduced the water activity to below 0.99, whereas liquid emollients alone did not. Example K further demonstrates that the crystalline emollients can be used in combination with fluid emollients and still reduce water activity. Emollients outside the scope of the invention (Table I) did not reduce the water activity.

EXAMPLE 2

This example illustrates the step-wise production of protease droplets which involves dispersal of powdered protease into the hydrophobic carrier such as petrolatum followed by emulsification to produce droplets of the hydrophobic carrier containing the protease. Three typical compositions of the enzyme-carrier droplets were prepared and are shown below:

| | | wt% | | |
|---|---|---|---|---|
| | Ingredient | A | B | C |
| Oil Phase | Enzyme (Optimase AP45, Solvay) | 1.7 | 2.2 | 2.2 |
| | Petrolatum (Snow White, Penereco) | 9.4 | 20 | 19.3 |
| | Silica (Cabosil, Cabot) | — | — | 0.7 |
| | Mineral Oil (Tro-grees, Penreco) | 11.1 | — | — |
| Xanthan Gum Phase | Xanthan Gum (Keltrol 1000, Kelco) | 1.67 | 1.67 | 1.67 |

-continued

| | | wt% | | |
|---|---|---|---|---|
| | Ingredient | A | B | C |
| | Glycerol (Dow) | 14.2 | 14.2 | 14.2 |
| | Propylene Glycol (Baker) | 2.5 | 2.5 | 2.5 |
| | Water | 16.5 | 16.5 | 16.5 |
| Polymer Phase | Acrylate polymer (Aculyn 33, Rohm and Haas) | 1.8 | 1.8 | 1.8 |
| | Water | 42.7 | 42.7 | 42.7 |

The step-wise procedure for the preparation of the above typical emulsions is described below:

1. Preparation of the Oil Phase

Petrolatum was melted and mixed with an overhead mixer. At 65°–70° C. the protease was added with rapid mixing and the heat was turned off. If optionally silica was desired as a viscosifying agent, it was added at this stage as well. The dispersion was allowed to cool with mixing. Progress was optionally added as a processing aid after the dispersion is cooled.

2. Preparation of the Polymer Phase and Xanthan Gum Phase

The polymer and xanthan gum phases were prepared as separate aqueous solutions. The polymer phase was neutralized with sodium hydroxide to pH 6.7. The xanthan gum phase was heated to 70° C.

3. Preparation of the droplets

The polymer phase was added to the oil phase and the mixture homogenized for 1 minute (Arde Barinco Homogenizer). The warm Xanthan gum solution was then added and the total mixture further homogenized for 2 minutes (Arde Barinco).

The above procedure produced droplets in the size range of 100–1000 uM in diameter as determined by microsocopy using an ocular micrometer. These enzyme droplets were then ready to be blended into the final emulsion.

EXAMPLE 3

This example illustrates that protecting protease enzyme from water, by incorporation into droplets as described in Example 2 and by adding the droplets to emulsions containing crystalline emollients which reduce the water activity to <0.99 as described in Example 1, increased storage stability.

Accelerated storage stability test

Aliquots of the enzyme-containing emulsions were dispensed into wide-mouth propylene bottles. The bottles were stored in a cabinet maintained at 30° C. At time intervals, samples were withdrawn and assayed for caseinolytic activity as described below.

Optimase was blended into emulsions from Example 1 as droplets (following Example 2C) or as raw powder. The caseinolytic activities obtained initially and at the indicated time interval based on the accelerated stability test are given in Table III below.

Assay for Caseinolytic activity

In all examples Caseinolytic Activity was expressed as glycine units (GU)/g emulsion. GUs were determined by measuring the rate of casein hydrolysis, as follows. Samples containing various quantities of a protease-containing emulsion were weighed into 16×100 mm test tubes. The weight of the emulsion sample should yield a final activity of 50–250 GU/g emulsion after dilution with assay buffer. (Example: A was a typical product containing about 12,000 GU/g, so about 0.15 9 of product was mixed with 10 ml of assay buffer.) The weight was recorded. 10 mL of assay buffer was added to each sample. Assay buffer was made fresh daily and contained 1% sodium sulfite, 0.5% sodium phosphate tripoly, 0.1% Synperonic A7 (ICI Surfactants) and 3.0% French Hardness solution (which contained 0.88% calcium chloride dihydrate, 0.61% magnesium chloride hexahydrate). Each sample was then homogenized into the buffer using a hand-held tissue homogenizer (Tissue Tearor, Biospec Products Inc.) at maximum speed for 30–60 seconds. 35 $\mu$L of each homogenate was then transferred to labeled microfuge tubes and mixed with 107 $\mu$L assay buffer, 73 $\mu$L of TNBS reagent (containing a 1:100 dilution of 10% 2,4,6-trinitrobenzenesulfonicacid (Research Organics Inc)) and 250 $\mu$L of casein substrate solution.

The casein substrate solution was prepared by mixing 16.2 g of sodium tetraborate decahydrate, 9.4 g sodium phosphate monobasic hydrate and 2 g N,N-diacetylcasein with 450 ml of water. After dissolving all constituents the pH was adjusted to 8.0 with 1N NaOH. While mixing, 0.5 ml of 30% Brij 35 was added and then the solution volume was adjusted to 500 ml with water. The final solution was then filtered through a Grade 6C50 borosilicate microfiberfilter (Microfiltration Systems Inc.).

Standard solutions having known caseinolytic activity of 0, 50, 100, 150, 200, and 250 GU/g of solution were prepared simultaneous to the preparation of product samples for assay. The standards were prepared with a certified Savinase standard prepared by Novo Nordisk. 35 $\mu$L of each standard were placed into labeled microfuge tubes and treated in the same fashion as the product samples.

After mixing all assay reagents together, the microfuge tubes were incubated for 70 minutes at 37° C. After incubation the tubes were removed and 250 $\mu$L of 20% trichloroacetic acid was added to each sample. Each tube was vortexed and then centrifuged at 10,000 rpm for 3–5 minutes in a microcentrifuge. 100 $\mu$L of the supernatant from each sample were then pipetted into wells of a 96 well plate and the intensity of yellow color was measured on a plate reader set to read absorbance at 410 nm. The enzyme activity (GU/g of emulsion) was calculated using the standard curve and the known dilution factor used in the assay.

The compositions of the emulsions, water activity, initial caseinolytic activity, and the percent of initial activity at indicated time intervals are shown in Table III. Samples 1 and 2 were within the scope of this invention. Samples 3 and 4 were outside the scope of this invention.

TABLE III

| Sample | Formula | Measured initial enzyme activity (GU/g emulsion) | Percent of Initial Activity | | | | |
|---|---|---|---|---|---|---|---|
| | | | Day 2 | Day 10 | Day 12 | Day 17 | Day 28 |
| 1 | 95% Emulsion H from example 1 +5% enzyme droplets C from example 2. (Aw = .984) | 19,689 | | 48.5 | 56.9 | 41.6 | |
| 2 | 95% Emulsion K from example 1 +5% enzyme droplets C from example 2 (Aw = .980) | 20,225 | | | | 115 | |
| 3 | 99.93% Emulsion H from example 1 + 0.07% raw (unencapsulated) enzyme (Aw = 0.984) | 15,806 | 16 | | | 8 | |
| 4 | 95% Emulsion E from example 1 +5% enzyme droplets B from example 2 (Aw = .993) | 21,930 | | 35.5 | 24 | 14.8 | |

The results in Table III demonstrate that storage stability was increased in samples 1 and 2 when the enzyme was incorporated into droplets and the enzyme droplets were incorporated into emulsions with Aw<0.99 which was achieved through the use of the crystalline emollients within the scope of the invention. The results also show that the incorporation of enzyme into a hydrophobic carrier within the scope of the invention (e.g., petrolatum) protected the enzyme from degradation. Furthermore, the stability was higher in formulations having a lower water activity due to the presence of crystalline emollients. Thus, according to the present invention, both the water activity and the incorporation of the protease into droplets are critical in order to stabilize protease in the inventive emulsions.

EXAMPLE 4

This example illustrates the effect of enzyme-containing emulsions on skin dryness. Enzyme-containing droplets and placebo droplets (not containing any enzyme) with compositions shown below were prepared using the procedure described in Example 2.

|  | Ingredient | wt % | |
|---|---|---|---|
|  |  | A | B (placebo) |
| Oil Phase | Enzyme (Optimase AP45, Solvay) | 2.2 | 0 |
|  | Petrolatum (Snow White, Penereco) | 19.3 | 21.5 |
|  | Silica (Cabosil, Cabot) | 0.7 | 0.7 |
|  | Mineral Oil (Tro-grees, Penreco) | — | — |
| Xanthan Gum Phase | Xanthan Gum (Keltrol 1000, Kelco) | 1.67 | 1.67 |
|  | Glycerol (Dow) | 14.2 | 14.2 |
|  | Propylene Glycol (Baker) | 2.5 | 2.5 |
|  | Water | 16.5 | 16.5 |
| Polymer Phase | Acrylate polymer (Aculyn 33, Rohm and Haas) | 1.8 | 1.8 |
|  | Water | 42.7 | 42.7 |

The droplets were then blended by hand into a typical emollient emulsion containing crystalline emollients which reduce the water activity, the composition of which is shown below.

| Ingredient | weight % |
|---|---|
| *Glycol stearate (Ritasynt IP, RITA Inc) | 1.50 |
| *Glycerol monostearate (Kessco GMS, Henkel) | 0.70 |
| *Cetyl phosphate (Monafax 160, Mona) | 0.25 |
| *Sodium stearoyl lactylate (RITA) | 0.10 |
| *Cetyl alcohol (Lanette 16, Henkel) | 0.40 |
| *Stearic acid (Pristerene 4911, Unichema) | 2.54 |
| Triethanolamine (Union Carbide) | 1.40 |
| Glycerol (Dow) | 5.50 |
| Carbomer (Carbopol 934, Union Carbide) | 3.00 |
| C11–C13 Isoparaffin (Isopar L, Exxon) | 2.00 |
| Sunflower seed oil (Tri-K Ind.) | 2.00 |
| Dimethicone (Dow) | 0.22 |
| Magnesium aluminum silicate (Van Der Bilt) | 0.20 |
| Water | qs to 100 |

*emollient within the scope of the invention

The level of protease incorporation and initial caseinolytic activity of the emulsion containing droplets A were 0.11 wt % and 14,433 GU/g respectively. The emulsion had a water activity of 0.976. The emulsion maintained greater than 50% of its initial activity after 14 days at 30° C.

The enzyme-containing and the placebo emulsions were examined for the effect on skin dryness according to the following procedure:

Clinical Procedure

The study was a balanced, randomized, double-blinded, complete block design with one cell of 25 female subjects. During the first five days of the study the subjects washed the test sites (lower legs) twice daily with Ivory soap to induce moderate dry skin. Subjects having a visually-determined dryness score of 2.0–3.5 were then qualified (on Monday) to enter into the treatment phase. These subjects then had 4 cm×5 cm test sites marked on each leg. Separate test sites were treated with either Example 4A or 4B. Product applications occurred on Tuesday PM and Wednesday AM & PM and Thursday AM & PM. Visual evaluations (using a Clinical Grading Index) were performed on Tuesday previous to application (Baseline), on Wednesday PM (Day 1), Thursday PM (Day 2) and Friday PM (Day 3).

|  | Mean Dryness Score | |
|---|---|---|
| Evaluation time point | Example 4A (enzyme-containing) | Example 4B (placebo) |
| Baseline (Day 0) | 2.6 | 2.6 |
| Day 1 | 2* | 2.7 |
| Day 2 | 1.6* | 2.6 |
| Day 3 | 1.4* | 2.3 |

*$p < 0.05$ (4A vs 4B)

The results show that the enzyme-containing emulsion significantly reduced the dryness compared to the placebo emulsion. Thus, the enzyme was still effective even after the incorporation of the enzyme into the droplets.

EXAMPLE 5

Example 5 illustrates that the skin dryness benefit of enzymes is dependent on the caseinolytic activity of the inventive emulsions in a dose dependent manner.

Four emulsions were prepared by adding enzyme droplets having different levels of enzyme (prepared as described in Example 2) to an emollient emulsion having the same composition as that described in example 4. The level of enzyme in each of these emulsions as well as the initial caseinolytic activity is shown below.

| Emulsion | Final protease concentration (%) in emulsion | Measured enzyme activity (initial; GU/g emulsion) |
|---|---|---|
| A | 0.083 | 14,989 |
| B | 0.012 | 2,391 |
| C | 0.0012 | 239.2 |
| D | 0 | 0 |

The skin dryness effect was examined as described in example 4 and the results are shown below.

|  | Mean Dryness Score | | | |
|---|---|---|---|---|
| Evaluation time | Example 5A 0.083% enzyme | Example 5B 0.012% enzyme | Example 5C 0.0012% enzyme | Example 5D 0% enzyme |
| Baseline | 2.72 | 2.70 | 2.82 | 2.78 |
| Day 1 | 1.91* | 2.23 | 2.41 | 2.45 |
| Day 2 | 1.36* | 1.73* | 2.30 | 2.36 |

*$p < 0.05$ vs 5D

The product with the highest enzyme activity (Example 5A) induced the greatest reduction in dryness compared to the other enzyme concentrations (Examples 5B and 5C). Furthermore, the presence of enzymes increased the dryness reducing ability of the emulsions (Examples 5A and 5B) compared to emulsion without enzyme (Example 5D).

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oil-in-water emulsion for a leave-on skin care composition the emulsion comprising:
   (a) from 1 wt % to 10 wt. % of droplets comprising a solid anhydrous protease distributed in a hydrophobic carrier, wherein the carrier has a melting point in the range of from 30° C. to about 80° C.;
   (b) at least 60% of water;
   (c) from 1 to 40 wt. % of an emollient which has a melting point in the range of from 30° C. to 80° C., wherein the emollient contains a hydrophobic hydrocarbon backbone and a hydrophilic polar headgroup, and wherein the emollient lowers the water activity of the emulsion to below 0.99.

2. The composition of claim 1, wherein the Caseinolytic Activity of the protease is at least 900 glycine unit per gram (GU/g) emulsion.

3. The composition of claim 1 wherein at least 10% of the Caseinolytic Activity of the protease is maintained on storage at an ambient temperature of 20°–25° C. for at least 6 months.

4. The composition of claim 1 wherein the protease:
   (1) has optimum activity between pH 5 and 9;
   (2) has specific activity greater than $8 \times 10^5$ GU/g of protease
   (3) has a broad substrate specificity as defined by an independence of specificity on primary structure.

5. The composition of claim 1 wherein the emulsion contains at least 80 wt. % water.

6. The composition of claim 1 wherein the emollient is selected from the group consisting of fatty acids, fatty alcohols, fatty acid esters of glycerol, fatty alcohol esters of glycerol, fatty alcohol esters of ethylene glycol, fatty alcohol esters of propylene glycol, fatty alcohol esters of lactyl lactate, and mixtures thereof.

7. The composition of claim 1, wherein the composition further contains a water-binding agent.

8. The composition of claim 6 wherein the water binding agent is selected from the group consisting of glycerol, a hydrophilic polymer, a clay, a gum, and mixtures thereof.

9. The composition of claim 1, wherein the size of the droplets ranges from about 100 μM to about 1,000 μM.

10. A cosmetic method of treating dry, flaky, cellulotic rough, aged, or wrinkled skin, the method comprising applying to the skin the composition of claim 1.

* * * * *